(12) United States Patent
Jiang

(10) Patent No.: US 9,474,629 B2
(45) Date of Patent: Oct. 25, 2016

(54) END PLATE SLIDER/DISTRACTOR FOR POSTERIOR INTERVERTEBRAL DEVICE AND METHOD

(75) Inventor: Hongxing Jiang, Edmonton (CA)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 392 days.

(21) Appl. No.: 12/806,709

(22) Filed: Aug. 19, 2010

(65) Prior Publication Data

US 2011/0071634 A1 Mar. 24, 2011

Related U.S. Application Data

(60) Provisional application No. 61/235,094, filed on Aug. 19, 2009.

(51) Int. Cl.

| A61B 17/58 | (2006.01) |
|---|---|
| A61B 17/60 | (2006.01) |
| A61F 2/00 | (2006.01) |
| A61F 2/46 | (2006.01) |
| A61B 17/02 | (2006.01) |
| A61F 2/44 | (2006.01) |
| A61B 17/88 | (2006.01) |
| A61B 17/68 | (2006.01) |

(52) U.S. Cl.
CPC .......... *A61F 2/4611* (2013.01); *A61B 17/025* (2013.01); *A61B 17/88* (2013.01); *A61F 2/4465* (2013.01); *A61B 2017/0256* (2013.01); *A61B 2017/0262* (2013.01); *A61B 2017/681* (2013.01); *A61F 2/4684* (2013.01); *A61F 2002/4615* (2013.01); *A61F 2002/4623* (2013.01); *A61F 2002/4625* (2013.01); *A61F 2002/4627* (2013.01); *A61F 2002/4629* (2013.01); *A61F 2002/4662* (2013.01)

(58) Field of Classification Search
CPC .......... A61B 17/1671; A61B 17/1757; A61F 2/4611
USPC .......... 606/90, 96, 99, 105, 86 A; 623/17.11–17.16
See application file for complete search history.

(56) References Cited

U.S. PATENT DOCUMENTS

| 3,486,505 | A | 12/1969 | Morrison |
| 5,431,658 | A | 7/1995 | Moskovich |
| 6,582,431 | B1 | 6/2003 | Ray |
| 6,652,533 | B2* | 11/2003 | O'Neil ............... A61F 2/4611 606/100 |
| 7,166,110 | B2 | 1/2007 | Yundt |
| 2002/0123753 | A1* | 9/2002 | Michelson .............. 606/90 |
| 2004/0002758 | A1* | 1/2004 | Landry et al. ......... 623/17.11 |
| 2004/0225295 | A1* | 11/2004 | Zubok ............... A61F 2/442 606/90 |
| 2006/0167461 | A1* | 7/2006 | Hawkins et al. ........ 606/90 |
| 2007/0123903 | A1* | 5/2007 | Raymond ......... A61F 2/4611 606/99 |
| 2007/0123904 | A1* | 5/2007 | Stad et al. .............. 606/99 |
| 2008/0275455 | A1* | 11/2008 | Berry ............... A61F 2/4611 606/99 |

* cited by examiner

*Primary Examiner* — Ellen C Hammond
*Assistant Examiner* — Christina Negrellirodrigue
(74) *Attorney, Agent, or Firm* — Greer, Burns & Crain, Ltd.

(57) ABSTRACT

A device and method for spreading apart adjacent vertebrae bodies for the safe insertion of an IBD into an IVD space said device designed for minimally invasive procedures and posterior or anterior approaches.

12 Claims, 7 Drawing Sheets

Figure 1. Working principle of the distraction and sliding

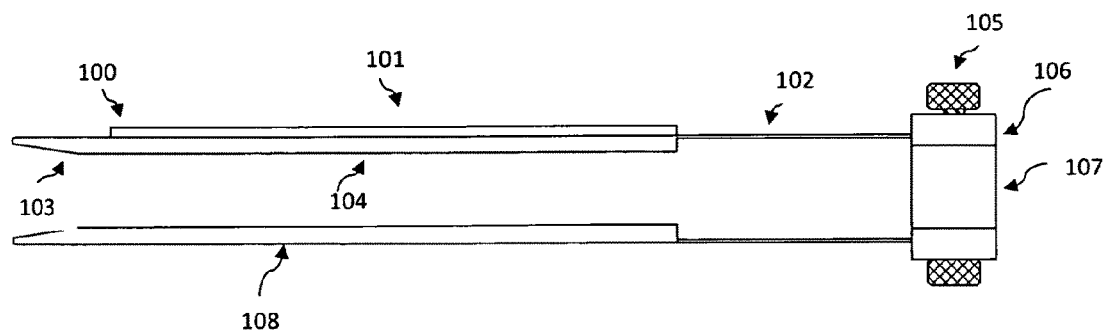
Figure 2-1
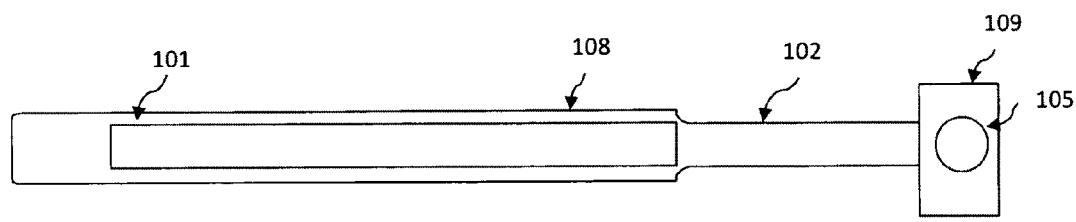
Figure 2-2
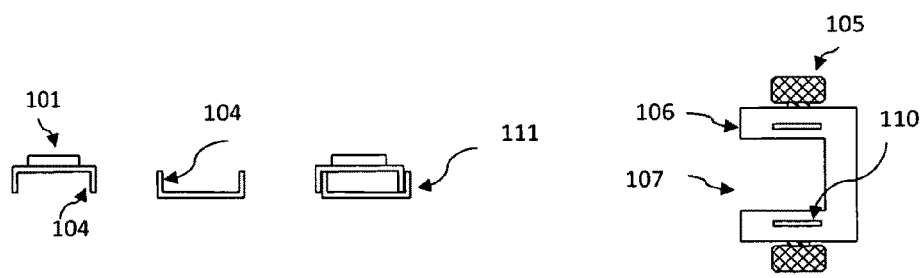
Figure 2-3                    Figure 2-4
Figure 2. Straight/flexible blades connected to a block handle Figure 3 Straight/rigid blades connected to a mobile handle with tilting capability

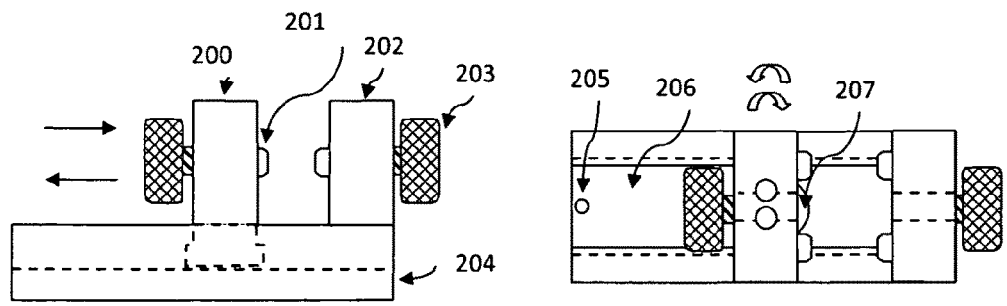
Figure 4-1. assembly of mobile handle with tilting capability
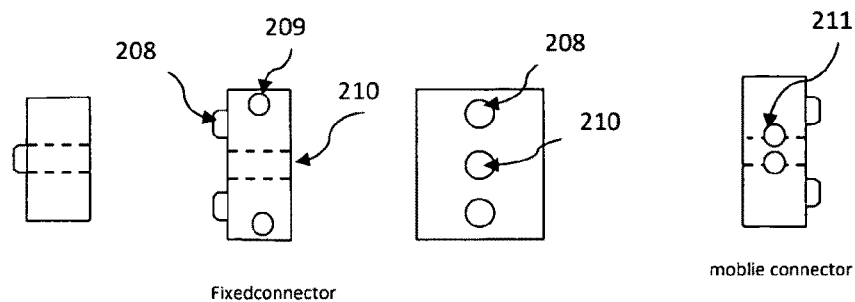
Fixedconnector
moblie connector
Figure 4-2. Left and right connectors. The left connectors is going to be connect to rotation block
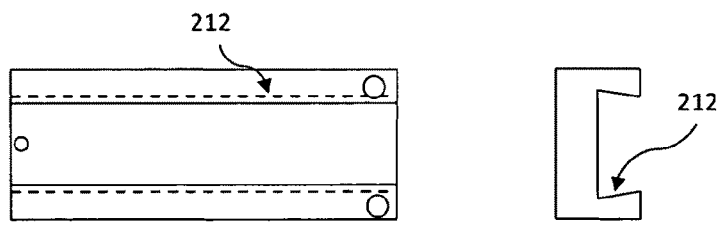
Figure 4-3. Handle sliding base
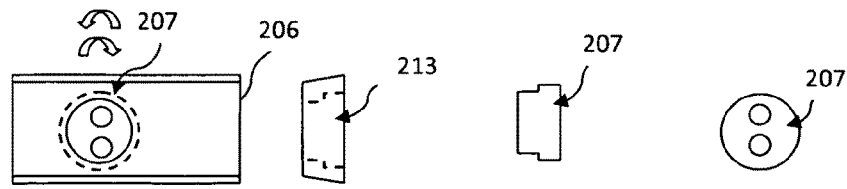
Figure 4-4. Sliding core with rotation block
Figure 4 Mobile handle with tilting capability

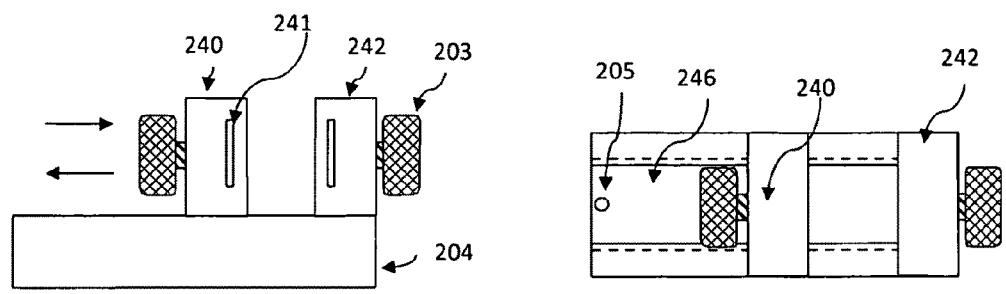
Figure 5-1 Assembly of a mobile handle
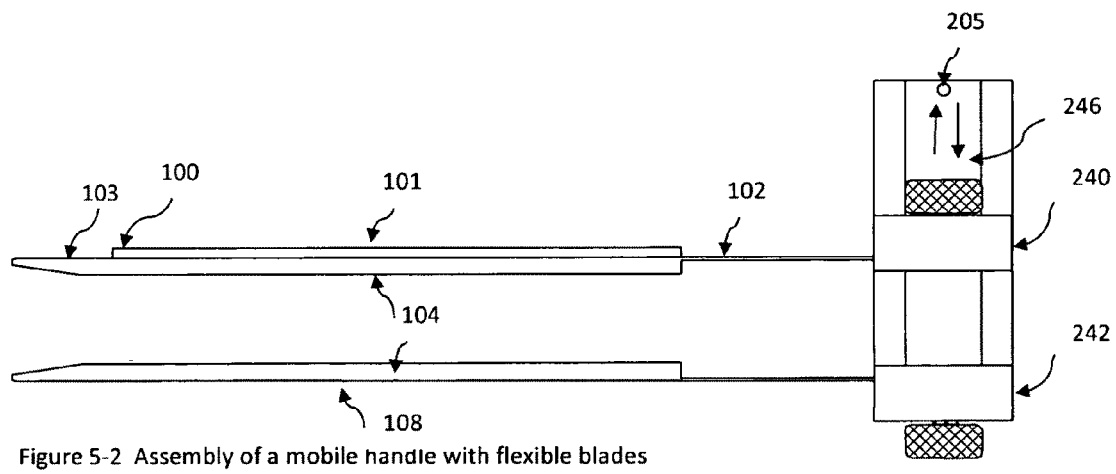
Figure 5-2 Assembly of a mobile handle with flexible blades
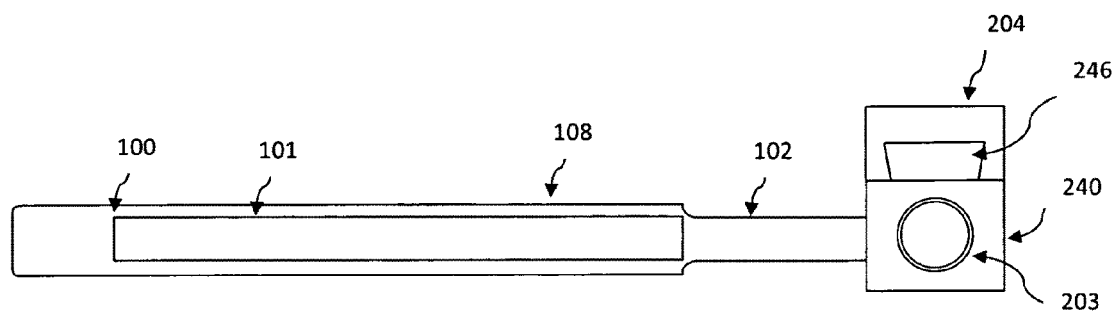
Figure 5-3 Assembly of a mobile handle with flexible blades in another view
Figure 5 A mobile handle without tilting capability connected to flexible blades

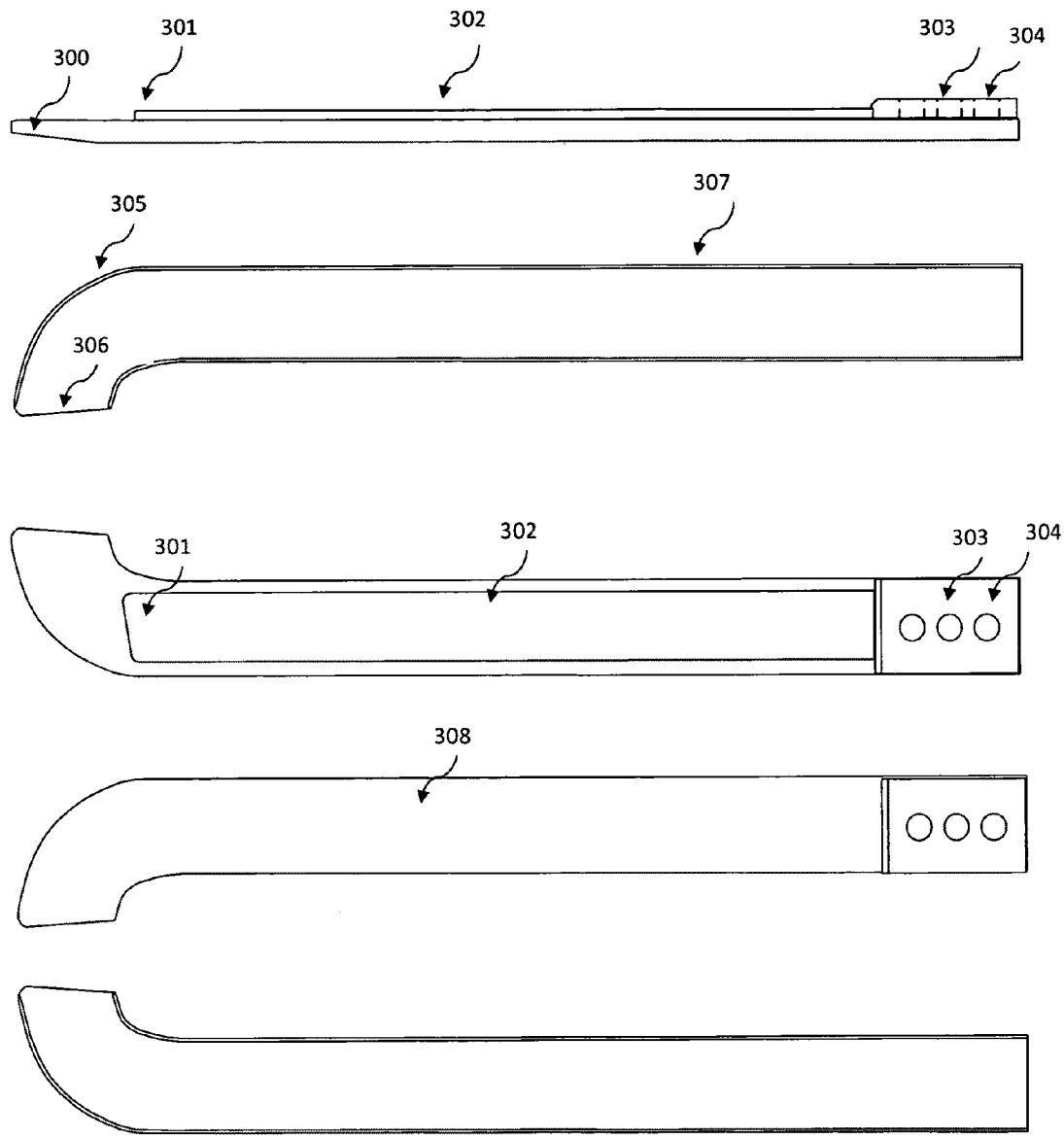
Figure 6. Curved and rigid blades

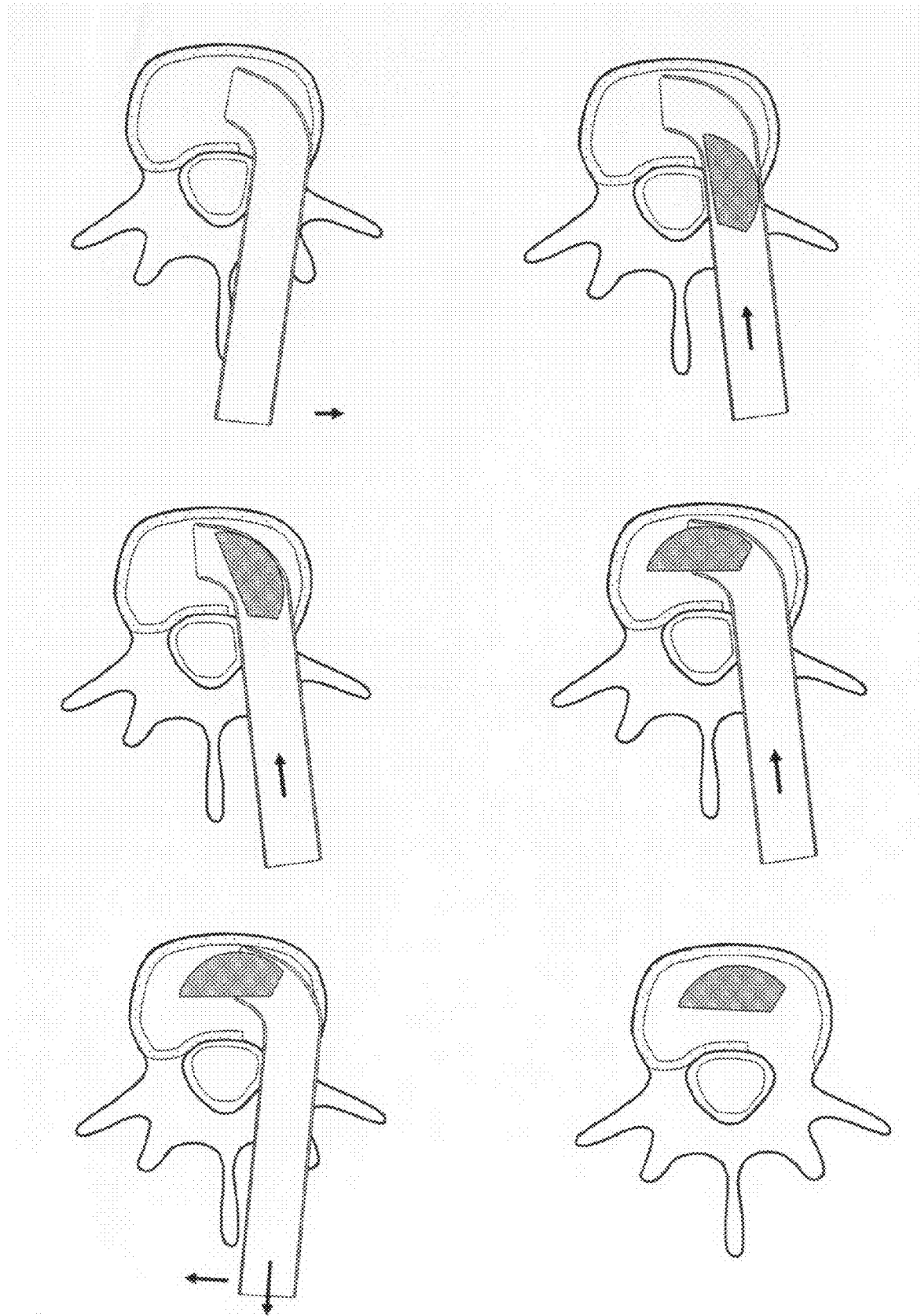
Figure 7. Application of curved distractor blade

END PLATE SLIDER/DISTRACTOR FOR POSTERIOR INTERVERTEBRAL DEVICE AND METHOD

RELATED APPLICATIONS

This application claims priority to U.S. Application No. 61/235,094, filed 19 Aug. 2009, the contents all of which are hereby incorporated by reference in their entirety.

FIELD OF INVENTION

The present invention relates to a device and method for spreading apart adjacent vertebrae bodies so that an intervertebral body device (IBD) may be safely inserted into the intervertebral disc (IVD) space. More particularly, the present invention relates to a distractor device designed to protect the endplates and surrounding soft tissue such as nerve roots and dura. This device is designed for minimally invasive procedures and can be used in all approaches such as posterior or anterior approaches. The IBD can be a device for fusion or for motion preserving procedures.

A distractor engages on end plates of adjacent vertebrae bodies for separation of the IVD. The distractor will separate the adjacent vertebrae bodies during the insertion of the IBD or its trial component. In the present invention, the distractor blades are winged on their inner sides. The wings will provide protection of the surrounding soft tissue such as superior nerve root and medial nerve root/dura for posterior procedures. The wings also function as a restraining track for the IBD path. The upper blade comprises a beam/stopper, the beam functioning as providing additional bending strength for the blades. The beams/stopper is on the top portion of the blades thereby not only providing extra bending strength to the superior blades but also functions as a stopper by preventing over insertion of the blade into the disc space. This beam/stopper may also provide measurement of the depth of insertion (in the coronal plane) of IBD into the intervertebral space.

The blades are versatile for different handles. In an embodiment, there are no wings or beams in the posterior portion of the blades, nearest the handles. The blades may be attached to a block handle. The partial length of the wings and beam will allow elastic movement of the blades in the sagittal plane which is necessary for the insertion of the IBD. In a further suitable embodiment, the wings and beams are of full length with reference to the blade. The blades are to be attached to a mobile handle. The movement of the blades in sagittal plane may be provided through the mobile handle. The blades may either be straight or curved for a variety of IBDs.

Posterior intervertebral fusion such as posterior lumbar interbody fusion (PLIF) and transforaminal lumbar interbody fusion (TLIF) are currently popular surgical procedures for treating patients with spine problems.

Traditionally, this procedure includes initial exposure of the spine followed by creation of a posterior lateral passage to the IVD. The IVD is removed to expose the end plate and the IVD space is then distracted with an IVD distraction device. The current IVD distraction devices do not allow insertion of the IBD while it is in the IVD space. This poses issues as the removal of the distraction device will lead to the intervertebral space collapsing back partially. A separate distraction device must then be applied to superior and inferior pedicle screws or spinus processes or laminar in order to open up the IVD space again for insertion of the IBD. This type of distraction method is less effective since it only applies distraction force on the posterior elements and not on the anterior element such as anterior longitudinal ligament and anterior annulus. Excessive amount of distraction may have to be applied to the posterior soft tissue, leading to the resulting distraction being often sub-optimal during this procedure. This may lead to difficulty in placing the IBD into the disc space or repositioning of the IBD into an ideal position. The IBD used in known methods also has a tendency to damage the vertebral body or end plate due to stress riser at the time of insertion causing sub-optimal recreation of IVD height and lordosis. The known distraction device is also bulky and not suitable for minimally invasive procedures.

Due to the limited access space of this procedure, the superior exiting nerve root, medial nerve root and dura sac are at risk of injury at the time of insertion of the IBD. The problems associated with insertion of the IBD put the patients who undergo such surgery at higher risk of complications or result in a smaller than planned device which may lead to sub-optimal clinical outcome. This type of surgery may even be acquitted during the surgical procedure if it is deemed to be too difficult or too risky by the surgeon due to possible damage to the nerve structure.

This background is provided for the purpose of making known information believed by the applicant to be of possible relevance to the present invention. No admission is necessarily intended, nor should it be construed, that any of the preceding information constitutes prior art against the present invention.

SUMMARY OF THE INVENTION

TLIF/PLIF procedures are popular spinal procedures in back surgery. These procedures can be very difficult and risky due to limited access to the intervertebral disk space and adjacent nerve structures i.e. superior nerve root and medial nerve root and dura sac. This invention will provide better access to the intervertebral disc space and increased protection to the nerve structure and end-plates. This device is also more minimally invasive as compared to the instruments currently being used such as aminar spreaders and pedicle screw spreaders. The latter are not minimally invasive and are less mechanically advantageous. They provide no protection to nerve roots and end plate-plates during the insertion process.

By using the invented device, the surgical procedure of inserting an IBD will become a safer and easier procedure and subsequently promote increased usage of IBDs.

The design of the device with a block handle is quite simple and production would be low cost. The device with a block handle may be disposable.

Currently, the IBDs being used are designed for easier insertion with a large bevel in the front part of the IBDs. Although this design may allow easier insertion of the IBDs, it sacrifices geographic matching of the IBD to that of end-plates. With the present device, the insertion of IBDs will be much easier and therefore the IBDs can be designed and manufactured for better matching to the end-plates.

Artificial disc replacement is another important procedure to for treating patients with back problems while preserving motion of the spine. The artificial discs currently being used are all implanted through an anterior approach. The anterior approach is associated with specific risks for complications. The artificial discs designed for posterior insertion are currently being researched and developed. The present device will provide better access and lower risk for future posterior inserted artificial discs.

It is an object of the present invention to obviate or mitigate at least one disadvantage of the prior art.

One aspect of the invention is directed to a device for distraction of adjacent vertebrae bodies including: an upper distraction blade and a lower distraction blade, the distraction blades adapted to engage end plates of the vertebrae bodies; a pair of side wings on the side of at least a portion of the distraction blades; and a beam/stopper (or beam-stopper) on a top portion of at least the upper blade. The blades and wings/beams define an inner confinement space for insertion of an intervertebral body device (IBD) or its trial component.

In one aspect of the present invention, there is provided a device for applying direct distraction of adjacent end-plates of vertebral bodies with minimized stress riser to the end-plates, provide guidance to the IBD during the insertion process and protect surrounding nerve structure. The device is compatible with a minimally invasive approach. The device is comprised of an upper sliding distraction blade and a lower sliding distraction blade with side tracks/wings; and a beam/stopper on the top side of the top blade. In one embodiment, the blades are flexible in their posterior portion allowing separation and approximation of the blades as well as tilting of the blades in a sagittal plane while the blades are attached to a block handle. In another embodiment, the blades are rigid with its top beam and side wings of substantially the same length as the blade itself. The rigid blades may be attached to a mobile handle; a handle functioning to connect the pair of blades as one unit. In one embodiment, the handle is made of one block of material. The block handle does not provide motion to the blades and the motion needed during the insertion of the IBD process is provided by the flexible portion of the blades itself. In another embodiment, the handle is designed with allowable motion of separation, approximation and tilting in a sagittal plane.

In a further aspect of the present invention, the anterior portion of the blades is made of thin and strong material. The blades are to cover a major portion of the whole depth of insertion track contacting the upper and lower end plate to reduce stress riser. This portion of blades may also be contoured to fit the geometry of end plates to avoid stress raiser further and over distraction during the insertion of an IBD. The surface of the blades should be smooth to allow easier insertion of the IBD and subsequent removal of the blades from the intervertebral space. The distraction is achieved by initial placement of the IBD or its trial between the two blades close to the vertebral bodies. A levering maneuver is then applied by closing the posterior portion of the blades together using the IBD or its trial as a fulcrum. The intervertebral space is then opened up partially. The IBD or its trial is then advanced further and this advancement will further distract the intervertebral space as needed.

In a yet further aspect of the present invention, the wings on the sides of the blades will provide three functions. They will provide partial strength to the blades to prevent bending of the blades during the levering maneuver. They will also act as tracks to allow proper positioning of the IBD. Finally, the wings will also provide protection to the nerve structures namely, the superior nerve roots, the medial dura sac and nerve root during the insertion process of an IBD. The beam/stopper on the superior aspect of the upper blade will provide further strength to the blade to prevent bending of the upper blade during the levering maneuver. The front end of the beam will provide engagement on the posterior corner of the upper vertebral body. The stopper will help control the depth of insertion for the device and allow measurement for the depth of insertion of the IBD. In another embodiment, the front end of the stopper can be oblique or curved depending on the planned insertion orientation of the IBD. In yet another embodiment, a second stopper on the inferior blade may be used. The front end of the beam/stopper can be straight, oblique or curved. The superior surface of the lower plate and the inferior surface of the upper plate should be smoothed out to allow better slide of the posterior intervertebral body device during the insertion process. This device may also not be coupled with the lower blade to avoid extra distraction of the intervertebral space during the insertion process.

In a yet further aspect of the present invention, there is provided a method of inserting an intervertebral body device (IBD) into an intervertebral disc (IVD) space between adjacent vertebral bodies including:
  inserting a device into an IVD space,
  placing of the IBD between the two blades close to the vertebral bodies,
  applying a levering maneuver by closing the posterior portion of the blades together so as to use the IBD as a fulcrum thereby opening the anterior portion of the blades and distracting the vertebral bodies.

In another aspect of the present invention, there is provided a method for spreading adjacent vertebrae bodies including:
  inserting a device into an intervertebral disc (IVD) space,
  placing of an intervertebral body device (IBD) between the two blades close to the vertebral bodies,
  applying a levering maneuver by closing the posterior portion of the blades together so as to use the IBD as a fulcrum thereby opening the anterior portion of the blades and distracting the vertebral bodies.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

FIG. 2-1 illustrates a top planar view of one embodiment of a pair of straight/flexible blades connected to a block handle of the present invention;

FIG. 2-2 illustrates a side-elevation view of an embodiment of the device of the invention with a top portion of a blade and handle;

FIG. 2-3 illustrates a front elevation view of the wings and beam/stopper of the one embodiment of the device of the present invention;

FIG. 2-4 illustrates a top planar view of one embodiment of the handle of the present invention;

FIG. 3-1 illustrates a top planar view of one embodiment of a pair of stiff blades connected to a mobile handle with sagittal tilting capability of the present invention;

FIG. 3-2 illustrates a side-elevation view of an embodiment of the invention with the top portion of a blade and a handle;

FIG. 3-3 illustrates a side-elevation view and a top elevation view of an embodiment of the invention;

FIG. 4-1 illustrates a cross-sectional exploded view of one embodiment of a mobile handle with sagittal tilting capability of the present invention;

FIG. 4-2 illustrates a cross-sectional view of connectors of handle in one embodiment of the present invention;

FIG. 4-3 illustrates a cross-sectional view of an embodiment of a mobile handle of the invention;

FIG. 4-4 illustrates a cross-sectional view of an embodiment of a mobile handle of the invention;

FIG. 5 illustrates one embodiment of a mobile handle connected to a pair of flexible blades of the present invention;

FIG. 6 illustrates a top planar view and side elevations views of embodiments of a pair of curved blades; and FIG. 7 illustrates a side view of the use of one embodiment of a curved distractor blade of the present invention.

DETAILED DESCRIPTION

This method and device of the invention include a set of two retraction blades 108 which can be engaged on the end plates of adjacent vertebral bodies to allow distraction of IVD space while inserting a posterior IBD or its trial component. This device will also help to define the orientation of the IVD space and allow smooth sliding of the IBD into the IVD space. By maintaining the contact area between the device and the end plate, the device may help avoid stress riser and prevent the IBD from cutting into vertebral body or damaging the end plates of the vertebral bodies during the insertion process.

The term "top" in relation to the blades is intended be in reference to the side facing the vertebral bodies when in use. The term "posterior" in relation to the portion of the blades refers to the portion nearest the handle or the portion protruding from the patient during use. The term "anterior" in relation to the portion of the blades refers to the portion for insertion into the IVD space.

Figure 1:
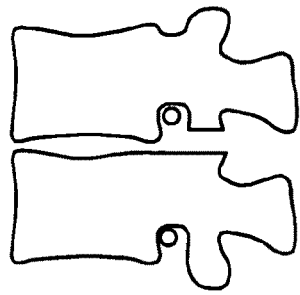
FIG. 1 illustrates a top planar view of the working principle of the present invention demonstrating the levering maneuver and one of the functions of the beam/stopper on a vertebral body.
Figures 1, 2:
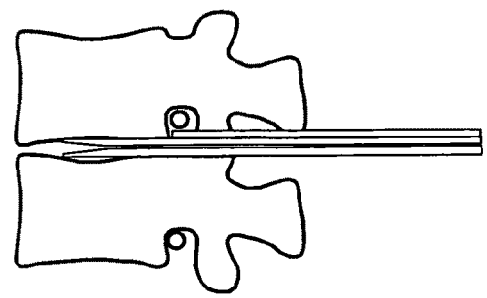
Figures 1, 2, 3:
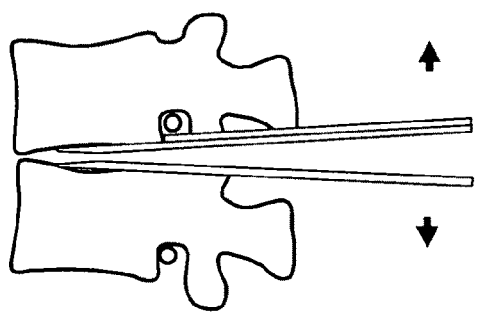

An appropriate surgical approach should be prepared first (FIG. 1-1), followed by removal of the disc material and initial distraction of the disc space. Over distraction of a few millimeters may be helpful. The device is then inserted with the tips of the blades approximated with the wings remaining side by side 111 (FIG. 2-3). The blades are thus thin enough for easier and safer insertion into the intervertebral space without blocking the view of the operation fields and endangering the nerve structures (FIG. 1-2). Because the blades 108 are thin, when being approximated the position of the blades can still be re-adjusted. The IBD or its trial component is then inserted through the inner confinement of the blades to a place adjacent to the vertebral body (FIG. 1-4). A levering maneuver is then applied by approximating the posterior portion of the blades 108 together with the IBD or its trial as the fulcrum. The maneuver will open up the anterior portion of the blades 108 and distract the IVD space (FIG. 1-5). The IBD or its trial component is then advanced within an inner confinement space defined by the wings/beams and tracks 104 to desired position with the wings protecting the surrounding nerves (FIGS. 1-5 and 1-6). After the IDD or its trial component is in place, the blades 108 can then be removed together with a slap hammer or individually to prevent shifting of the IBD while the blades are being removed.

There is a beam/stopper (101/100) on the top portion of the top blade. The beam 101 will provide more bending strength to the top blade and prevent bending of the top blade during the levering and insertion process. The stopper 100 will also engage on the posterior-inferior corner of the upper vertebral body during the insertion of the IBD. This stopper 100 can provide measurement of depth of the insertion of the blades and the IBD. This stopper 100 will also prevent unwanted over insertion of the blades and the IBD during the insertion process.

A pair of side wings 104 are presently folded on at least a portion of either side of the longitudinal length of the blades. The wings 104 are designed to act as a pair of beams to provide bending strength of the blade during the levering and insertion process. The wings 104 are also designed to provide protection of the medial nerve root/dura sac and the superior nerve root. Instead of potential impact on the nerve structure without the use of this device, only gradual stretching will be applied to the medial nerve root/dura sac and the superior root during the insertion process with the device, thus preventing damage to the aforementioned nerve structure (FIG. 2). The wings 104 will also act as tracks to guide the IBD towards the intended position. The pair of wings can be manufactured by either folding thin materials at the sides of the blades or by machining thick materials. The tips of the wings 104 are suitably beveled 103 to allow more approximation of the upper and the lower blades 108.

The blades used can be rigid or flexible. In an embodiment of the flexible blades 108, there are no wings over the posterior portion of the blades 102. The posterior portion the blades 102 will allow some elastic deformation of the blades in the sagittal plane. The tips of the blades thus can be approximated or separated when the pair of flexible blades are attached to a solid block handle 106 during the insertion process of the IBD. The anterior and posterior portion of the blades can also be treated, such as heat treated, differently so that the strength of the anterior portion can be increased and the posterior portion of the blades can be more elastic. The approximation of the tips of the blades 111 will help insertion of the blades into the IVD space. The separation of the blades is needed for the distraction process. In one embodiment, a handle is reversibly attachable to the blades. Suitably, flexible blades are connected to the block handle through a hole 131 in the posterior end of the blade.

When the handle is a block handle, it is conceived that the blades may be flexible in their posterior portion allowing separation and approximation of the blades as well as tilting of the blades in a sagittal plane while the blades are attached to the block handle. In embodiments wherein the handle is a mobile handle, it is conceived that the blades are rigid and that the side beams may be of substantially the same length as the blades.

Figures 1, 2, 3, 4:
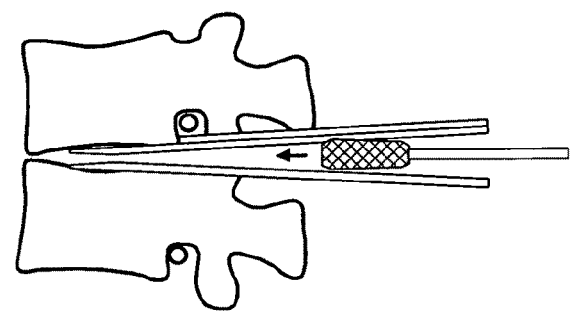
Figures 1, 2, 3, 4, 5:
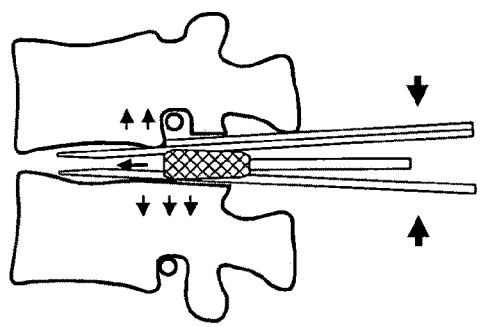

For the embodiment of the rigid blades 112, the wings 104 and the beam 101 are typically in full or nearly in full length with the blades. This embodiment will allow more levering arm during the insertion process of the IBD. The rigid blades are typically connected to a mobile handle allowing for a larger motion in approximation, separation of the blades and more lever arm for distraction (FIGS. 3 and 4). In one embodiment, the blades 112 are connected to the mobile handle with tilting capability 204 through one threaded hole 122 and two smooth holes 121. In another embodiment, the blades 112 may also connected to a mobile handle without tilting capability 250.

Figures 1, 2, 3, 4, 5, 6:
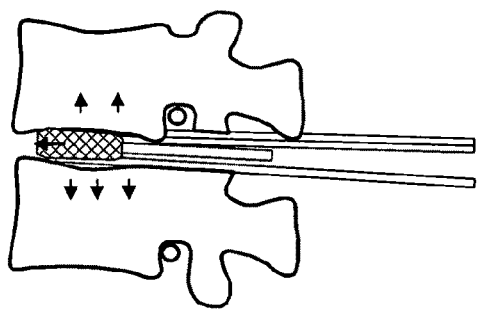
Figures 1, 2, 3, 4, 5, 6, 7:
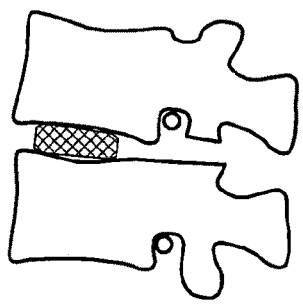
Figures 1, 3:
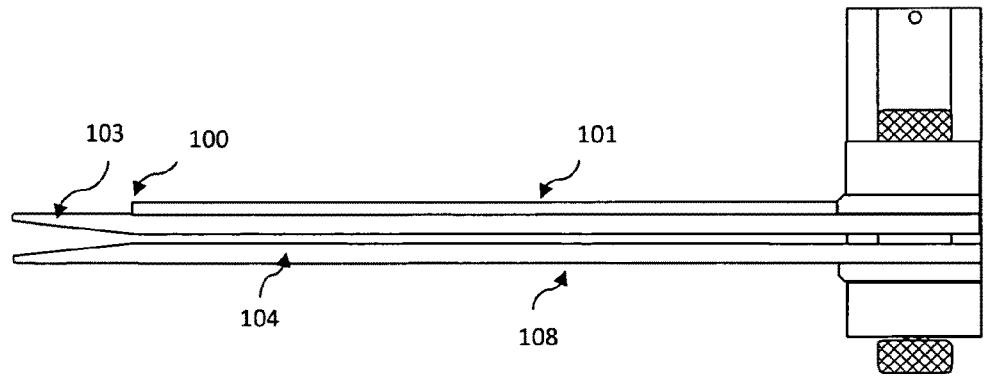
Figures 2, 3:
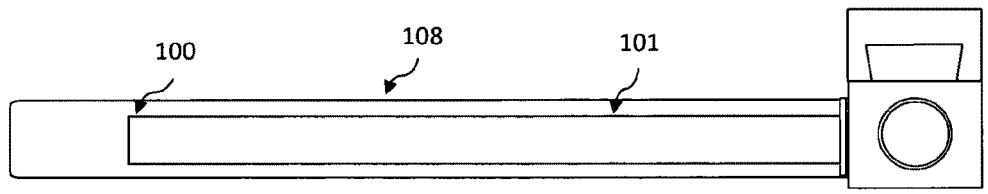
Figure 3:
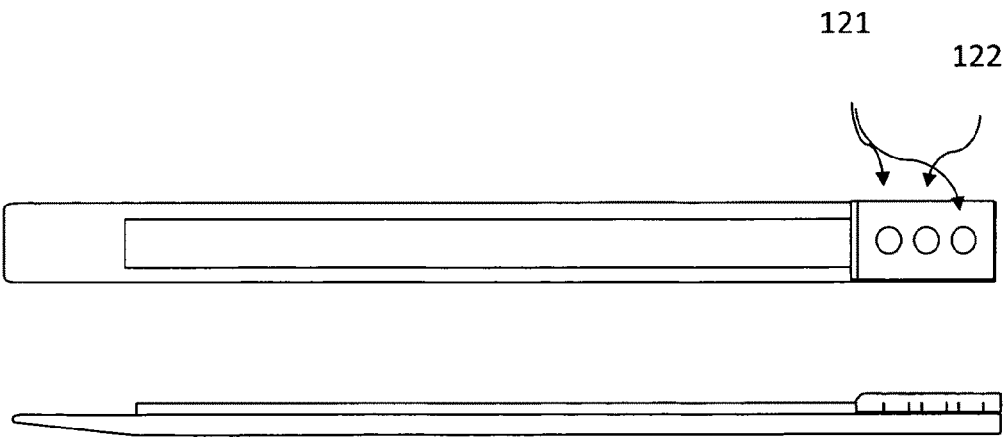

In one embodiment, the blades 308 can also be curved in the front part 305 to provide tracks for insertion of a larger and more medialized IBD from one side only (FIG. 6 and FIG. 7). The curved track 305 will provide guidance for the IBD to move into an intended position. Similar to the straight blades, the wings of the curved blades may add strength to the blade and also provide protection to the surrounding nerve structures while the IBD is being inserted. In one embodiment, the front end of the blades can be oblique 306 to prevent extra stretching to the medial nerve and dura. In another embodiment, a stopper 301 may also be oblique to provide better fit to the posterior edge of the upper vertebra body.

The block handle 106 allows quick attachment/detachment of the pair of flexible blades of particular dimension to the handle itself through a thin slot 110 and a thumb screw 105. In one embodiment, the flexible blade is secured to the thumb screw through a hole. In another embodiment, one side of the block is open 107 to allow minimal view obstruction of surgical field and side movement of other insertion tools. This will be particularly useful when using curved blades for insertion of the IBD and removal of the blades. The open end block will allow for insertion of an IBD bigger than the middle slot of the block and hence permit a smaller design of the block handle for minimally invasive procedures. A series of different dimensions of the blocks may be needed to fit the IBDs with different height.

In one embodiment of the mobile handle with tilting capability 204, the handle allows quick attachment of the pair of rigid blades of particular dimension by means of one thumb screw 203 and two dowels 208. There are two connectors on the handle. The fixed connector 202 is attached to one end of the handle base. The mobile connector 200 is attached to a rotation block 207 and the rotation block is located in the sliding core 206 to allow sagittal tilting of the mobile connector. The sliding core is then inserted into the handle base 212 to allow changing of the distance between the fixed and mobile connectors. One side of the block is open to allow minimal view obstruction of surgical field and side movement in respect to other insertion tools. This will be particularly useful when using curved blades while inserting the IBD and removing of the blades. This design will allow a bigger range of the dimensions of the IBD. This design will also allow the use of rigid blades which will provide more cantilever effect during the process of IBD insertion.

In another embodiment of the mobile handle, the handle can be simplified to function without tilting capability 250. In this embodiment, the mobile connector 240 will be directly fixed to the sliding core 246. A slot 241 and a thumb screw 203 will be used to connect the flexible blades to the mobile handle 250.

Other embodiments and uses of the invention will be apparent to those skilled in the art from consideration of the specification and practice of the invention disclosed herein. The specification and examples should be considered exemplary only and do not limit the intended scope of the invention.

What is claimed is:

1. A device for distraction of adjacent vertebrae bodies comprising:
   an upper distraction blade and a lower distraction blade, said blades each including a length, an outer side, an inner side, and opposing edges that are transverse to said outer side and said inner side, wherein said inner sides face each other and are substantially flat, said blades adapted to engage end plates of the vertebrae bodies;
   a pair of side wings extending along said inner sides of at least a portion of said blades and transversely projecting from a planar surface defined by said inner sides of said blades;
   a beam-stopper on said outer side of one of said blades; and
   a handle reversibly attachable to said blades, wherein said handle is a block handle, said blades are flexible in a posterior portion to allow separation and approximation of said blades as well as tilting of said blades in a sagittal plane while said blades are attached to said block handle, and said side wings each have a length that is substantially the same as the length of the blades.

2. The device according to claim 1 wherein said blades, pair of wings and beam-stopper define an inner confinement space for insertion of a distracting wedge or an intervertebral body device (IBD) component.

3. The device according to claim 1, wherein the wings have tips which are beveled to allow more approximation of the upper and the lower blades.

4. The device according to claim 1, wherein anterior and posterior portions of said blades are made differently so as to increase the strength of said anterior portion and to increase the elasticity of said posterior portion of the blades.

5. The device according to claim 1, wherein said blades are substantially straight.

6. The device according to claim 1, wherein said blades are curved in a front portion so as to provide tracks for inserting an IBD from one side only.

7. The device according to claim 1, wherein said beam-stopper is oblique or curved.

8. A method of inserting an intervertebral body device (IBD) into an intervertebral disc (IVD) space between adjacent vertebral bodies comprising:
   inserting a device according to claim 1 into an IVD space;
   placing of the IBD between two blades close to the vertebral bodies; and
   applying a levering manoeuvre by closing the posterior portion of the blades together so as to use the IBD as a fulcrum thereby opening an anterior portion of the blades and distracting the vertebral bodies.

9. The method according to claim 8, wherein the IBD is subsequently advanced within wings, beams and tracks to a desired position thereby further distracting the intervertebral space.

10. A method for spreading adjacent vertebrae bodies comprising:
    inserting a device according to claim 1 into an intervertebral disc (IVD) space and then forcing in a distracting wedge between the two blades.

11. A device for distraction of adjacent vertebrae bodies comprising:
    an upper distraction blade and a lower distraction blade, said blades each including a length, an outer side, an inner side, and opposing edges that are transverse to said outer side and said inner side, wherein said inner sides face each other and are substantially flat, said blades adapted to engage end plates of the vertebrae bodies, and wherein anterior and posterior portions of said blades are made differently so as to increase the strength of said anterior portion and to increase the elasticity of said posterior portion of the blades;
    a pair of side wings extending along said inner sides of at least a portion of said blades and transversely projecting from a planar surface defined by said inner sides of said blades;
    a beam-stopper on said outer side of one of said blades; and
    a handle reversibly attachable to said blades, wherein said handle is a mobile handle, said blades are rigid, and said side wings each have a length that is substantially the same as the length of the blades.

12. A device for distraction of adjacent vertebrae bodies comprising:
    an upper distraction blade and a lower distraction blade, said blades each including a length, an outer side, an inner side, and opposing edges that are transverse to said outer side and said inner side, wherein said inner sides face each other and are substantially flat, said blades adapted to engage end plates of the vertebrae bodies;

a pair of side wings extending along said inner sides of at least a portion of said blades and transversely projecting from a planar surface defined by said inner sides of said blades;

a beam-stopper on said outer side of one of said blades; and a handle reversibly attachable to said blades, wherein said handle is a block handle, said blades are flexible in a posterior portion to allow separation and approximation of said blades as well as tilting of said blades in a sagittal plane while said blades are attached to said block handle through a hole in said posterior portion of said blades, and said side wings each have a length that is substantially the same as the length of the blades.

* * * * *